United States Patent [19]

Tatsuoka et al.

[11] Patent Number: 4,766,116
[45] Date of Patent: Aug. 23, 1988

[54] DIARYL BUTYRIC ACID DERIVATIVE AND PHARMACEUTICAL USE THEREOF

[75] Inventors: Toshio Tatsuoka, Nishinomiya; Kenji Suzuki, Osaka; Kayoko Imao, Ikoma; Kunihiro Sumoto, Oonojo, all of Japan

[73] Assignee: Suntory Limited, Osaka, Japan

[21] Appl. No.: 810,591

[22] Filed: Dec. 19, 1985

[30] Foreign Application Priority Data

Dec. 21, 1984 [JP] Japan .................. 59-268549

[51] Int. Cl.$^4$ ................. A61K 31/165; C07C 103/82; C07C 103/84
[52] U.S. Cl. .................... 514/218; 514/255; 514/329; 514/330; 514/354; 514/415; 514/423; 514/532; 514/563; 514/567; 514/622; 514/227.5; 514/237.5; 514/237.8; 514/238.8; 514/239.2; 540/575; 544/58.3; 544/164; 544/168; 544/176; 544/382; 544/383; 544/388; 544/390; 544/396
[58] Field of Search ............... 540/575; 544/58.2, 164, 544/168, 176, 382, 383, 388, 390, 396; 546/224, 226, 234, 306, 307, 337; 548/483, 493, 571; 560/58; 564/171, 174; 562/441; 514/218, 222, 234, 255, 329, 330, 354, 415, 423, 532, 563, 567, 622

[56] References Cited

U.S. PATENT DOCUMENTS

4,007,282  2/1977  Mauz et al. .................. 564/174 X
4,645,853  2/1987  Stephen et al. ................... 560/58

FOREIGN PATENT DOCUMENTS

41732    1/1966   Japan .
50-24276  3/1975   Japan .
5219672  12/1975   Japan .
55-17329  2/1980   Japan .
58-110547 7/1983   Japan .

Primary Examiner—Richard L. Raymond
Attorney, Agent, or Firm—Burns, Doane, Swecker & Mathis

[57] ABSTRACT

A diaryl butyric acid derivative having the general formula:

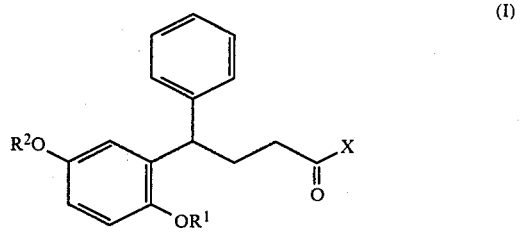

(I)

wherein
R$^1$ represents a hydrogen atom, an alkyl group having 1 to 3 carbon atoms, or an acyl group having 2 to 4 carbon atoms; R$^2$ represents an alkyl group having 1 to 3 carbon atoms; and
X represents a variety of substituents.

This diaryl butyric acid derivative or the pharmaceutically acceptable salt thereof can be prepared by reacting a benzoxepin derivative having the general formula:

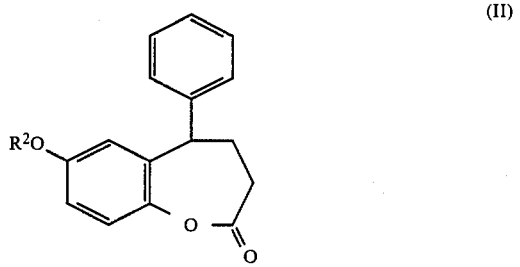

(II)

wherein R$^2$ is the same as defined above with an amine or alcohol derivative having the general formula;

X—H wherein X is the same as defined above in the presence of an acid catalyst at room temperature or at an elevated temperature and, optionally, further reading the reaction product with an alkylation agent having 1 to 3 carbon atoms or an acylation agent having 2 to 4 carbon atoms.

This diaryl butyric acid derivative or the pharmaceutically acceptable salt thereof is effective for ameliorating or treating various symptoms based on cerebral organic disorders and pathergasia.

12 Claims, No Drawings

DIARYL BUTYRIC ACID DERIVATIVE AND PHARMACEUTICAL USE THEREOF

BACKGROUND OF THE INVENTION

1. Field of the Invention

The present invention relates to a novel diaryl butyric acid derivative and the pharmaceutically acceptable salt thereof as well as a production process thereof. More specifically, it relates to a diaryl butyric acid derivative or the pharmaceutically acceptable salt thereof which is effective for ameliorating and curing (or treating) various symptoms based on cerebral organic disorders (or cerebral dysfunction or brain (organic) syndrome) and pathergasia.

The term "cerebral organic disorders" used herein means various symptoms derived from cerebral ischemic disorders or diseases such as cerebral infarct sequela, cerebral hemorrhage sequela, and cerebral arteriosclerosis sequela and various organic disorders derived from senile dementia, dementia presenilis, amnesia, cephalic traumatic sequela, and cerebral operation sequela. Furthermore, the term "pathergasia" used herein means psychogender organic diseases like mania, melancholia, neurosis, Parkinson's disease, schizophrenia, schizophrenia-like disorders, and chorea (or Huntington's chorea) as well as various syndromes derived from medicines and alcoholic beverages.

2. Description of the Related Art

Cerebral cells retain their own intracellular environments which are completely different from the surrounding environments, i.e., extracellular fluids, and while this difference is maintained, cerebral cells are alive. For this reason, it is necessary for energy to be always generated and supplied to cerebral cells. Most of the energy required by cerebral nerve cells is supplied by oxygen and glucose. These energy sources are not substantially stored in the brain and, therefore, are always to be supplied from the blood.

If certain cerebral disturbances or disorders occur, and if the supply of oxygen and glucose to the brain is stopped, generally there is a gradual or stepwise progression in energy cacochimia. As a result, the cells lose their functions with the elapse of time, and the cells are soon organically broken. Thus, the cerebral cells cannot effect their normal functions. Therefore, a mechanism to adjust cerebral bloodstreams in the cerebral blood vessels themselves has been fully developed to stably supply the energy sources to the cerebral tissues and to maintain the outer environments of cerebral nerve cells.

Various cerebral circulation ameliorating agents (or circulating improvers), cerebral vasodilators, and cerebral excitometabolites have been heretofore used for the medical treatment of cerebral blood vessel disorders. However, although these medicines are effective for ameliorating subjective symptoms, no substantial amelioration in neural symptoms and mental symptoms are observed. Of these medicines, it is reported in, for example, Japanese Unexamined Patent Publication (i.e., Kokai Nos. 58-110547 and 55-17329 and Japanese Examined Patent Publication (Kokoku) No. 41-732 that 4-amino butyric acid derivatives are considered to be effective for curing dementia and amnesia. Furthermore, it is proposed in, for example, Japanese Unexamined Patent Publication (Kokai) Nos. 50-24276 and 52-19672 that diaryl butyric acid derivatives are useful as medicines for treatment of central nervous system disorders.

In addition, although various medical studies have been made into the amelioration and cure of senile dementia, there still remain many problems to be solved because of the presence of various psychogender functional symptoms. For this reason, families and other persons must take great care when nursing these patients, which need becomes a serious social problem.

SUMMARY OF THE INVENTION

An object of the present invention is to provide a novel compound having effective activities for ameliorating and curing (or treating) various symptoms caused by the above-mentioned various cerebral disorders or brain syndromes.

Other objects and advantages of the present invention will be apparent from the following description.

In accordance with the present invention, there is provided a diaryl butyric acid derivative having the general formula:

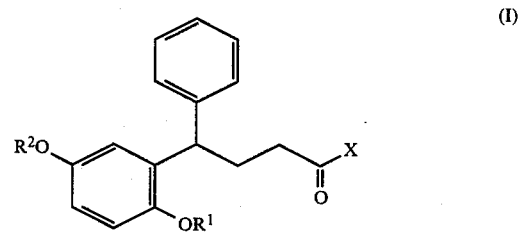

wherein
- $R^1$ represents a hydrogen atom, an alkyl group having 1 to 3 carbon atoms, or an acyl group having 2 to 4 carbon atoms;
- $R^2$ represents an alkyl group having 1 to 3 carbon atoms; and
- X represents a pyrrolidinyl group, a morpholino group, a thiomorpholino group, an amino group, and a group having the general formula:

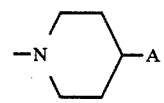

wherein A represents a hydrogen atom or an alkyl group having 1 to 3 carbon atoms,
a group having the general formula:

wherein J represents a phenyl group, a benzyl group, a aralkyl group having 7 to 9 carbon atoms substituted with at least one hydroxyl group,
a group having the general formula:

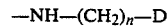

wherein n is an integer of 0 to 5, D represents a saturated crosslinked ring type hydrocarbon group, a piperidinyl group, a morpholino group, a thiomorpholino group, a pyridyl group, an indolyl group, a piperazinyl group, a pyrrolidinyl group, a carboxyl group, a phenyl group substituted with a hydroxyl, or aryloxy group, an N-[4-(2'-hydroxy-5'-methoxy)phenyl-4-phenylbutyryl]piperazinyl group, or a piperazinyl group having an alkyl group with 1 to 3 carbon atoms substituted for the hydrogen atom on the nitrogen atom, a group having the general formula:

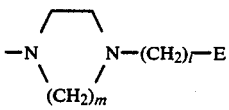

wherein m is 2 or 3, l is an integer of 0 to 4, E is a hydrogen atom, a phenyl group, a hydroxyl group, a pyrrolidinecarbonyl group, a 4-(4,'-methoxyphenyl)-4-phenylbutylamide group, or a 4-(2'hydroxy-5'-methoxy) phenyl4-phenylbutyryl group, a group having the general formula:

wherein p is an integer of 2 to 4, and L represents a dialkylamino group having a $C_1$-$C_3$ alkyl group, or a group having the general formula:

wherein G represents an aralkyl group having 8 to 9 carbon atoms substituted with at least two hydroxyl groups;

or the pharmaceutically acceptable salt thereof.

DESCRIPTION OF THE PREFERRED EMBODIMENTS

The diaryl butyric acid derivatives having the above-mentioned general formula (I) and the pharmaceutically acceptable salts thereof according to the present invention have an antilipid peroxidation activity and are extremely effective for remedying oxygen deficit conditions of various cerebral nerve cells (i.e., cerebral anoxia). That is, the diaryl butyric acid derivatives having the general formula (I) and the pharmaceutically acceptable salts (i.e., sometimes "diaryl butyric acid derivatives") according to the present invention are active against test animals having cerebral anoxia at a low dose and, therefore, are an effective remedy for the oxygen deficit conditions of various cerebral nerve cells. The diaryl butyric acid derivatives according to the present invention also have an antilipid peroxidation activity. Thus, the diaryl butyric acid derivatives or the pharmaceutically acceptable salts thereof are effective for ameliorating and curing various psychogender functional symptoms caused by cerebral organic disorders.

The diaryl butyric acid derivatives having the general formula (I) can be synthesized as follows. That is, a benzoxepin derivative having the general formula:

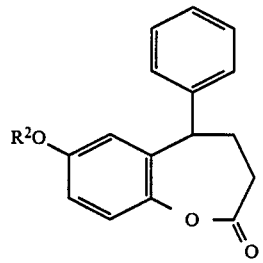

wherein $R^2$ is the same as defined above
is reacted with an amine or alcohol having the general formula

X—H, wherein X is the same as defined above preferably in an amount of one mole or more based on 1 mole of the compound (II), in the presence of an acid catalyst at room temperature or an elevated temperature and, optionally, the reaction product is further reacted with an alkylation agent having 1 to 3 carbon atoms or an acylation agent having 2 to 4 carbon atoms, and optionally, further followed by treatment with a pharmaceutically acceptable acid.

For example, a known compound, γ-phenyl-γ-butyrolactone having a melting point of 36° C. to 37° C. is reacted with a phenol derivative having the general formula:

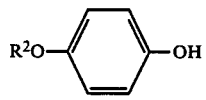

wherein $R^2$ represents a hydrogen atom or an alkyl group having 1 to 3 carbon atoms in the presence of a base such as sodium alkoxide, potassium alkoxide, sodium hydroxide, potassium hydroxide, sodium hydride, or sodium metal to form a 4-phenyl butyric acid derivative having the general formula:

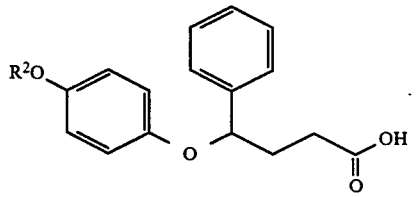

wherein $R^2$ is the same as defined above,

The 4-phenyl butyric acid derivative (IV) is then subjected to a rearrangement reaction and a dehydrating cyclization reaction under an acidic condition to form 5-phenyl-2-oxo-benzoxepin having the general formula (II) at a good yield.

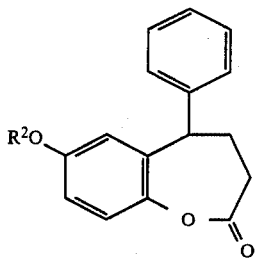

(II)

wherein R² is the same as defined above,

In this reaction, an acid such as polyphosphoric acid, phosphoric acid, sulfuric acid, p-toluenesulfonic acid, aluminum chloride or phosphorus pentoxide can be preferably used to obtain the desired compound (II) at a high yield. The compound (II) can be also obtained by reacting the phenol derivative (III) directly with the above-mentioned γ-phenyl-γ-butyrolactone in the presence of the above-mentioned acid.

The benzoxepins (II) obtained above are novel compounds. The benzoxepin (II) ia reacted, in the presence of a catalytic amount of an acid, with an amine or alcohol having the general formula;

X—H wherein X is the same as defined above at room temperature or an elevated temperature (or a heating conditions) to obtain the present compound having the general formula:

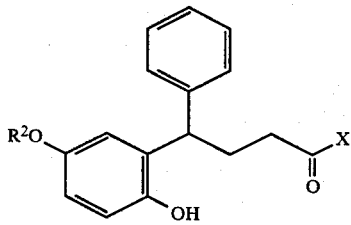

(Ia)

wherein R² and X are the same as defined above.

The acid catalysts preferably used in this reaction include, for example, p-toluenesulfonic acid, benzenesulfonic acid, sulfuric acid, camphorsulfonic acid, boron trifluoride, and naphthalene-β-sulfonic acid. The reaction of the benzoxepin (II) with the amine or alcohol having the general formula X—H can be preferably carried out in an organic solvent such as benzene, toluene, xylene, anisole, octane, dioxane, tetrahydrofuran, 1,2- dimethoxyethane, 1,2-diethoxyethane, diethylene glycol dimethyl ether, chlorobenzene, dichloroethane, trichloroethane, chloroform, and methylene chloride at a temperature of, preferably, 50° C. to 180° C., the reaction of the above-mentioned compound (II) with the amine or alcohol having the general formula X—H can be carried out by, for example, mixing both the components, followed by heating to reflux. Thus, the present compounds (Ia) can be obtained. Although there are no critical limitations to the reaction time, the reaction is preferably carried out for about 4 hours to 3 days.

The present compounds (Ia) obtained above can be treated with pharmaceutically acceptable acids in any conventional manner. Examples of such acids are hydrochloric acid, sulfuric acid, phosphoric acid, hydrobromic acid, acetic acid, trifluoroacetic acid, succinic acid, oxalic acid, malic acid, propionic acid, fumaric acid, maleic acid, and tartaric acid.

The above-mentioned compounds (Ia) according to the present invention can be treated with an alkylating agent having 1 to 3 carbon atoms (e.g., diazomethane, diazoethane, or diazopropane) or an acylating agent (e.g., acetic anhydride, propionic anhydride, acetyl chloride, propionyl chloride, butyryl chloride, or butyric anhydride) to form the other diaryl butyric acid derivatives according to the present invention having the general formula;

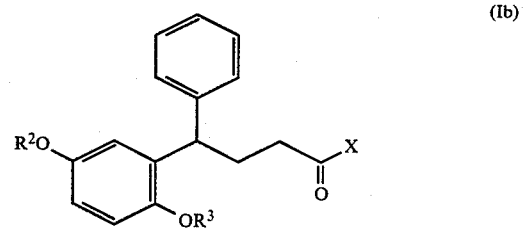

(Ib)

wherein R² and X are the same as defined above and R³ is an alkyl group having 1 to 3 carbon atoms or an acyl group having 2 to 4 carbon atoms.

The compounds (Ib) can be treated with the above-mentioned pharmaceutically acceptable acids to form the pharmaceutically acceptable salts thereof in the same manner as in the compounds (Ia).

The novel diaryl butyric acid derivatives (I) and the pharmaceutically acceptable salts thereof according to the present invention are effective for ameliorating and curing various symptoms based on cerebral organic disorders and pathergasia. This is clear from the below-mentioned Evaluation Examples because the present compounds (I) are effective for test animals having various cerebral anoxia and have excellent antilipid peroxidation activity against such test animals.

When the present diaryl butyric acid derivatives are used as a medicine, there are no critical limitations to the administration methods.

For parenteral administration, the compounds of the present invention are converted into water soluble salts thereof and the salts are dissolved in sterile distilled water or sterile physiological saline and are filled in ampules to be used for injection. If necessary, stabilizing agents and/or buffering agents can be included in the ampules.

The compounds of the present invention can be administered alone or in combination with excipients in a variety of dosage forms such as tablets, troches, pills, granules, powders, capsules, ampules, suppositories and the like. The excipients include, for example, starch, dextrin, sucrose, lactose, silic acid, carboxymethylcellulose, cellulose, geratin, polyvinylpyrrolidone, glycerin, agar, calcium carbonate, sodium bicarbonate, paraffin, cetyl alcohol, stearic acid esters, kaolin, bentonite, talc, calcium stearate, magnesium stearate, polyethyleneglycol, water, ethanol, isopropyl alcohol, propyleneglycol and the like.

For oral administration, the optimum dose range of the compounds of the present invention is 0.5 to 500 mg per day. Of course, this dose range can be suitably changed depending upon the characteristics of the subjects including age, response, weight, severity of disease and the like.

EXAMPLES

The present invention now will be further illustrated by, but is by no means limited to, the following Synthesis Examples and Evaluation Examples.

Synthetic Example 1

Preparation of 4-(2-hyddroxy-5-methoxy)phenyl-4-phenyl-1-(4-methyl)piperazinyl-1-oxobutane To 2.68 g (0.01 mol) of 7-methoxy-5-phenyl-2-oxo-2,3,4,5-tetrahydro-1-benzoxepin in chlorobenzene solution, an excess amount of N-methyl-piperazine was added and the mixture was then heated to reflux for 5 hours. After the reaction mixture was cooled, the reaction mixture was diluted with ether and was then extracted with a 2N aqueous sodium hydroxide solution. The extracted solution was neutralized with 2N hydrochloric acid, followed by extracting with ether. After the extracted solution was dried with anhydrous magnesium sulfate, the dried solution was filtered and concentrated and the resultant residue was separated and purified by a silica gel column chromatography. Thus, the desired product was isolated in 85% yield. The desired compound having the following properties was further obtained by recrystallization from acetone.

Mass spectrum (m/z): 368 (M$^+$),

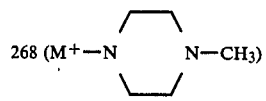

268 (M$^+$—N⌒N—CH$_3$)

IR spectrum: $\nu_{C=O} = 1600$ cm$^{-1}$,
$\nu_{OH} = 3150$ cm$^{-1}$

The other properties of the resultant compounds are as shown in Table 1.

Synthetic Examples 2 to 18

7-Methoxy-5-phenyl-2-oxo-2,3,4,5-tetrahydro-1-benzoxepin was dissolved in chlorobenzene or toluene and was then reacted with various amines in the same manner as in Example 1. Thus, the desired compounds shown in Table 1 were obtained.

The results are as shown in Table 1.

Synthetic Example 19

Preparation of 4-(2-hydroxy-5-methoxy)phenyl-4-phenyl-1-(2-piperidinyl)ethylamino-1-oxobutane hydrochloride 7-Methoxy-5-phenyl-2-oxo-2,3,4,5-tetrahydro-1-benzoxepin was reacted with 2-piperidinyl ethylamine in the same manner as in Example 1. After purification, the product was dissolved in ethanol and ether saturated with gaseous hydrogen chloride was added thereto. The precipitated crystal was recrystallized to give the desired compound in 64% yield.

The results are as shown in Table 1.

Synthesis Examples 20 to 40

The compounds according to the present invention were prepared by using various amines in the same manner as in Example 19.

The results are as shown in Table 1.

Synthesis Example 25

Preparation of 4-(2-hydroxy-5-methoxy)phenyl-4-phenyl butyrylamide

A 2.68 g (10 mmol) amount of 7-methoxy-5-phenyl-2-oxo-2,3,4,5-tetrahydro-1-benzoxepin was stirred at room temperature for 3 hours in 50 ml of ethanol saturated with ammonia. After concentration, the residue was separated and purified by a silica gel column chromatography. Thus, the desired compound was isolated in 90% yield. The product was recrystallized from acetone-petroleum ether.

The results are as shown in Table 1.

Synthesis Example 26

Preparation of 4-(2-hydroxy-5-methoxy)phenyl-4-phenyl-1-(N-methyl-N-phenyl)amino-1-oxobutane A chlorobenzene solution of 2.68 g (10 mmol) of 7-methoxy-5-phenyl-2-oxo-2,3,4,5-tetrahydro-1-benzoxepin and a two equivalent amount of N-methylaniline was heated to reflux for 3 days. After concentration, the residue was separated and purified by a silica gel column chromatography. The desired compound was isolated in 70% yield.

The results are as shown in Table 1.

Synthesis Example 27

Preparation of 4-(2-hydroxy-5-methoxy)phenyl-4-phenyl-1-[N-(4-hydroxy-4-oxo)butyl]amino-1-oxobutane To a dioxane solution of 1.34 g (5 mmol) of 7-methoxy-5-phenyl-2-oxo-2,3,4,5-tetrahydro-1-benzoxepin, benzyl γ-amino butyrate.p-toluene sulfonic acid salt and triethylamine were added. The mixture was heated to reflux to obtain 4-[2-hydroxy-5-methoxy)phenyl-4-phenyl-1-(N-(4-benzyloxy-4-oxo)butyl]amino-1-oxobutane in 72.7% yield.

The resultant product was then catalytically reduced in the presence of palladium-black in dioxane to obtain the desired compound in 77% yield. The resultant compound was recrystallized from ether to give the pure compound in 56% yield.

The results are as shown in Table 1.

Synthesis Examples 28 and 29

Preparation of 4-(2-hydroxy-5-methoxy)phenyl-4-phenyl-1-piperazinyl-1-oxobutane (Example 28) and N,N'-bis[(4-(2-hydroxy-5-methoxy)phenyl-4-phenyl)-1-oxobutyl]piperazine (Example 29)

A 2.68 g amount of 7-methoxy-5-phenyl-2-oxo-2,3,4,5-tetrahydro-1-benzoxepin and one equivalent amount of piperazine were heated to reflux in chlorobenzene for 5 hours. After concentration, the residue was separated and purified by a silica gel column chromatography. Thus the desired compounds of Synthesis Examples 28 and 29 were obtained in amounts of 1.62 g (yield=46%) and 969 mg (yield=16%), respectively.

The results are as shown in Table 1.

Synthesis Examples 30 and 31

Preparation of 4-(2-hydroxy-5-methoxy)phenyl-4-phenyl-1-homopiperazinyl-1-oxobutane (Example 30) and N,N'-bis-[(4-(2-hydroxy-5-methoxy)phenyl-4-phenyl)-1-oxobutyl]homopiperazine (Example 31)

A 2.68 g amount of 7-methoxy-5-phenyl-2-oxo-2,3,4,5-tetrahydro-1-benzoxepin and an excess amount of homopiperazine were heated to reflux in toluene for 16 hours. After concentration, the residue was separated and purified by a silica gel column chromatography. Thus, 1.2 g (35% yield) of the desired compound (Example 30) and 1.97 g (31% yield) of the desired compound (Example 31) were obtained.

The results are as shown in Table 1.

Synthesis Examples 32 and 33

Preparation of 4-(2-hydroxy-5-methoxy)phenyl-1-[(2-piperazinyl)ethyl]amino-1-oxobutane (Example 32) and 4-(2-hydroxy-5-methoxy)phenyl-1-[4-(2-(4-(2-hydroxy-5-methoxy)phenyl-4-phenyl-1-oxo)aminoethyl)-piperadinyl]-1-oxobutane (Example 33)

A 2.68 g amount of 7-methoxy-5-phenyl-2-oxo-2,3,4,5-tetrahydro-1-benzoxepin and an excess amount of N-(2-amino)ethylpiperazine were heated to reflux in toluene for 16 hours. After concentration, the residue was separated and purified by a silica gel column chromatography. Thus, 1.03 g (26% yield) of the desired compound (Example 32) and 1.19 g (18% yield) of the desired compound (Example 33) were obtained. The compounds of Examples 32 and 33 were converted into their hydrochloride salts and the hydrochlorides were then recrystallized from ethanol-ether.

The results are as shown in Table 1.

Synthesis Example 34

Preparation of 4-(2-acetoxy-5-methoxy)phenyl-4-phenyl-2-(4-methyl)-piperazinyl-1-oxobutane A 1.1 g (3 mmol) amount of the compound obtained in Synethsis Example 1 was dissolved in pyridine and an excess amount of acetic anhydride was added thereto. The mixture was stirred at room temperature for 4 hours. After the reaction mixture was concentrated, ether was added thereto and the mixture was washed with aqueous sodium bicarbonate solution. The ether layer was further washed with water, followed by drying. After concentration, the residue was subjected to a silica gel column chromatography to give the desired compound in 95% yield. The crystalline product thus obtained was recrystallized from benzene-petroleum ether to afford its pure form as colorless crystals.

The results are as shown in Table 1.

Synthesis Example 35

Preparation of 4-(2,5-dimethoxy)phenyl-4-phenyl-1-(4-methyl)-piperazinyl-1-oxobutane.hydrochloride A 412 mg (1.1 mmol) amount of the compound obtained in the Synthesis Example 1 was dissolved in 200 ml of a mixed solvent of ether-ethanol (3:1) and 4 g of silica gel and an excess amount of diazomethane were added thereto. The mixture was stirred at room temperature overnight.

The reaction mixture was filtered and concentrated. The residue was purified by a silica gel column chromatography to give 210 mg (49% yield) of the desired compound. The compound thus obtained was dissolved in ether and the ether saturated with gaseous hydrogen chloride was added thereto to give its hydrochloride salt.

The results are as shown in Table 1.

Synthesis Example 36

Preparation of 4-(2-hydroxy-5-methoxy)phenyl-4-phenyl-1-(2-dimethylamino)ethyloxy-1-oxybutane A 2.68 g (10 mmol) amount of 7-methoxy-5-phenyl-2-oxo-2,3,4,5-tetrahydro-1-benzoxepin was dissolved in dioxane and 1.2 equivalent amount of dimethylamino ethanol and a catalytic amount of p-toluenesulfonic acid were added thereto. The mixture was heated under reflux for 5 hours. The reaction mixture was concentrated and the residue was subjected to a silica gel column chromatography. Thus, the desired compound was obtained in 81% yield.

The results are as shown in Table 1.

The physical properties of the compounds obtained in the Synthesis Examples 1 to 36 are shown in Table 1.

In Table 1, the IR spectra were measured in the form of a potassium bromide tablet in the case of the crystal and in the form of a film in the case of the oily substance. The NMR spectra were measured in deuterated chloroform (i.e., $CDCl_3$) unless otherwise noticed. The data of the IR spectra, the NMR spectra, the mass spectra, and the elementary analysis in Table 1 are those of the free compounds unless otherwise noticed.

TABLE 1

[Structure: phenyl-CH(Ph)-CH2-CH2-C(=O)-X with a benzene ring bearing OR¹ and OR² substituents]

| Example No. | Compound | Yield % | Properties (Recrystallization solvent) | IR spectrum ($v_{max} cm^{-1}$) | NMR spectrum (CDCl₃, $\delta_{ppm}$) | (a) Elementary analysis or (b) High resolution mass spectrum |
|---|---|---|---|---|---|---|
| 1 | R¹ = Hydrogen<br>R² = methyl<br>X = N—Methyl-piperazinyl | 85 | m.p. 173.0–174.0° C. (acetone) | 1600<br>3150 | 2.22–2.45 (m, 8H), 2.29 (s, 3H), 3.30–3.45 (m, 2H), 3.53–3.77 (m, 2H), 3.62 (s, 3H), 4.32 (m, 1H), 6.26 (d, 1H, J = 3.5Hz), 6.62 (dd, 1H, J = 3.5, 7.8Hz), 6.86 (d, 1H, J = 7.8Hz), 7.17–7.42 (m, 5H), 8.52 (brs, 1H) | (b) as C₂₂H₂₈N₂O₃<br>Calc.: 368.2099<br>Found: 368.2086 |
| 2 | R¹ = hydrogen<br>R² = methyl<br>X = morpholino | 90 | m.p. 172.0–173° C. (acetone) | 1605<br>3250 | 2.20–2.40 (m, 4H), 3.37 (m, 2H), 3.61 (m, 2H), 3.62 (s, 4H), 3.67 (s, 3H), 4.31 (dd, 1H, J = 6.0, 7.0Hz), 6.27 (d, 1H, J = 3.0 Hz), 6.64 (dd, 1H, J = 9.0, 3.0Hz), 6.86 (d, 1H, J = 9.0Hz) 7.21–7.40 (m, 5H) | (a) as C₂₁H₂₅NO₄<br>Calc.: C 70.96 H 7.09 N 3.94<br>Found: 70.89 7.13 3.89 |
| 3 | R¹ = hydrogen<br>R² = methyl<br>X = piperidino | 73.8 | m.p. 203.5–204.0° C. (acetone) | 1590<br>3150 | 1.42–1.70 (m, 6H), 2.20–2.35 (m, 4H), 3.20–3.77 (m, 4H), 4.33 (t, 1H, J = 6.8Hz), 6.23 (d, 1H, J = 3.1Hz), 6.62 (dd, 1H, J = 3.1, 9.3Hz), 6.88 (d, 1H, J = 9.3Hz), 7.11–7.40 (m, 5H), 8.84 (s, 1H) | (a) as C₂₂H₂₇NO₃<br>Calc.: C 74.76 H 7.70 N 3.96<br>Found: 75.05 7.78 4.10 |
| 4 | R¹ = hydrogen<br>R² = methyl<br>X = N—phenyl piperadinyl | 85 | m.p. 148.0–149.0° C. (ethanol) | 1620<br>3250 | 2.23–2.46 (m, 4H), 3.07–3.22 (m, 4H), 3.48–3.59 (m, 2H), 3.62 (s, 3H), 3.75–3.95 (m, 2H), 4.34 (t, 1H, J = 6.0Hz), 6.29 (d, 1H, J = 3.7Hz), 6.64 (dd, 1H, J = 9.2Hz), 6.83–6.99 (m, 4H), 7.20–7.42 (m, 7H), 8.31 (s, 1H) | (a) as C₂₇H₃₀N₂O₃<br>Calc.: C 73.08 H 7.61 N 5.88<br>Found: 72.84 7.56 5.90 |
| 5 | R¹ = hydrogen<br>R² = methyl<br>X = N—benzyl piperadinyl | 72.3 | m.p. 171.0–172.0° C. (acetone) | 1600<br>3130 | 2.20–2.50 (m, 8H), 3.45 (m, 2H), 3.50 (s, 2H), 3.60 (s, 3H), 3.60–3.75 (m, 2H), 4.32 (brt, 1H), 6.35 (d, 1H, J = 3.1Hz), 6.63 (dd, 1H, J = 3.1, 8.4Hz), 6.88 (d, 1H, J = 8.4Hz) 7.16–7.40 (m, 5H), 8.58 (s, 1H) | (a) as C₂₈H₃₂N₂O₃<br>Calc.: C 75.64 H 7.26 N 6.30<br>Found: 75.31 7.31 6.25 |
| 6 | R¹ = hydrogen<br>R² = methyl<br>X = N—benzyl-N—methyl-amino | 94.3 | Isomer mixture (3:2) | 1603<br>3200 | 2.2–2.5 (m, 4H), 3.61 (s, 3H), 3.82 (s, 3H), 4.30–4.45 (m, 1H), 4.55 (d, 1H, J = 14.8Hz), 4.73 (d, 1H, J = 14.8Hz), 6.20–6.30 (m, 1H), 6.55–6.70 (m, 1H), 6.89 (d, 1H, J = 8.6Hz) | (a) as C₂₅H₂₇NO₃<br>Calc.: C 77.09 H 6.99 N 3.60<br>Found: 76.92 6.97 3.65 |
| 7 | R¹ = hydrogen<br>R² = methyl<br>X = N—(2-hydroxyethyl) piperazinyl | 78.4 | m.p. 90.5–91.5° C. (acetone-petroleum ether) | 1620<br>3320 | 2.20–2.40 (m, 4H), 2.4–2.6 (m, 6H), 3.66–3.43 (m, 2H), 3.62 (s, 3H), 3.63–3.80 (m, 4H), 4.32 (t, 1H, J = 6.2Hz), 6.21 (d, 1H, J = 3.1Hz), 6.63 (dd, 1H, J = 3.1, 8.9Hz), 6.87 (d, 1H, J = 8.9Hz), | (a) as C₂₃H₃₀N₂O₄<br>Calc.: C 69.32 H 7.59 N 7.03<br>Found: 69.69 7.42 6.37 |

TABLE 1-continued

![Structure: phenyl-CH(Ar)-CH2-CH2-C(=O)-X where Ar is 2,5-bis(OR)phenyl with R2O and OR1]

| Example No. | Compound | Yield % | Properties (Recrystallization solvent) | IR spectrum ($\nu_{max}$ cm$^{-1}$) | NMR spectrum (CDCl$_3$, $\delta_{ppm}$) | (a) Elementary analysis or (b) High resolution mass spectrum |
|---|---|---|---|---|---|---|
| 8 | R$^1$ = hydrogen<br>R$^2$ = methyl<br>X = thiomorpholino | 97.0 | m.p. 191.0–192.0° C. (acetone-petroleum ether) | 1603<br>3200 | 7.17–7.40 (m, 5H), 8.43 (s, 1H)<br>2.20–2.40 (m, 4H), 2.40–2.75 (m, 4H),<br>3.61 (s, 3H), 3.50–3.75 (m, 2H),<br>3.75–4.10 (m, 2H), 4.28 (t, 1H, J = 7.4Hz)<br>6.28 (d, 1H, J = 3.2Hz), 6.63 (dd, 1H,<br>J = 3.2, 9.4Hz), 6.87 (d, 1H, J = 9.4Hz)<br>7.15–7.40 (m, 5H), 8.26 (br.s, 1H) | (a) as C$_{21}$H$_{25}$NO$_3$S<br>　　C (%) H (%) N (%) S (%)<br>Calc.: 67.91 6.79 3.77 8.62<br>Found: 68.04 6.81 3.77 8.57 |
| 9 | R$^1$ = hydrogen<br>R$^2$ = methyl<br>X = N—(pyridine-2-yl) methylamino | 84.0 | m.p. 189.0–190.0° C. (acetone-petroleum ether) | 1640<br>3300 | 2.05–2.35 (m, 4H), 3.63 (s, 3H),<br>4.20–4.40 (m, 3H), 6.58 (dd, 1H, J = 2.7,<br>8.6Hz), 6.68 (d, 1H, J = 8.6Hz), 6.78 (d,<br>1H, J = 2.7Hz), 7.05–7.35 (m, 7H),<br>7.65–7.80 (m, 1H), 8.34 (t, 1H, J = 5.9Hz),<br>8.40–8.55 (m, 1H), 8.90 (br.s, 1H) | (a) as C$_{23}$H$_{24}$N$_2$O$_3$<br>　　C (%) H (%) N (%)<br>Calc.: 73.38 6.43 7.44<br>Found: 73.47 6.48 7.50 |
| 10 | R$^1$ = hydrogen<br>R$^2$ = methyl<br>X = 4-methyl-piperidino | 62.1 | m.p. 199.5–200.5° C. (acetone) | 1590<br>3150 | 0.92–0.97 (m, 3H), 0.98–1.16 (m, 1H),<br>1.52–1.73 (m, 4H), 2.20–2.36 (m, 4H),<br>2.52–2.65 (m, 1H), 2.86–2.99 (m, 1H),<br>3.61 (s, 3H), 3.63–3.73 (m, 1H), 4.33 (t,<br>1H, J = 6.3Hz), 4.60–4.70 (m, 1H), 6.23 (d,<br>1H, J = 3.1Hz), 6.63 (dd, 1H, J = 3.1,<br>8.8Hz), 6.89 (d, 1H, J = 8.8Hz) | (a) as C$_{23}$H$_{29}$NO$_3$<br>　　C (%) H (%) N (%)<br>Calc.: 75.17 7.95 3.81<br>Found: 75.36 8.05 3.83 |
| 11 | R$^1$ = hydrogen<br>R$^2$ = methyl<br>X = N—methyl-N—2-hydroxy-2-(3',4'-dihydroxyphenyl) ethylamino | 73.1 | m.p. 65.0–67.5° C. (benzene) | 1603<br>3300 | In d$_6$-dimethylsulfoxide | |
| 12 | R$^1$ = hydrogen<br>R$^2$ = methyl<br>X = N—morpholinoamino | 56.1 | m.p. 94.0–95.0° C. (ethanol-ether) | 1700<br>3300 | 2.30–2.65 (m, 4H), 3.3 (s, 3H), 3.30–4.20<br>(m, 2H), 3.98 (s, 3H), 4.5–4.65 (m, 1H),<br>4.65–4.95 (m, 1H), 6.6–7.2 (m, 6H),<br>7.4–7.75 (m, 5H)<br>2.0–2.90 (m, 8H), 3.63 (s, 3 H), 3.40–3.90<br>(m, 4H), 4.12 (t, 1H, J = 3.3Hz), 6.40 (d, 1H,<br>J = 3.3Hz), 6.60 (dd, 1H, J = 3.3, 8.7 Hz),<br>6.80 (d, 1H, J = 8.7Hz), 7.15–7.40 (m, 5H) | (a) as C$_{21}$H$_{26}$N$_2$O$_4$·HCl<br>　　C (%) H (%) N (%) Cl (%)<br>Calc.: 61.98 6.69 6.89 8.71<br>Found: 61.99 6.77 6.88 8.66 |
| 13 | R$^1$ = hydrogen<br>R$^2$ = methyl<br>X = pyrrolidinyl | 88.5 | m.p. 162.0–163.0° C. (acetone-ether) | 1590<br>3150 | 1.81–1.98 (m, 4H), 2.24–2.33 (m, 4H),<br>3.27–3.34 (m, 4H), 3.47–3.57 (m, 4H),<br>3.61 (s, 3H), 4.41 (t, 1H, J = 5.2Hz), 6.24<br>(d, 1H, J = 3.2Hz), 6.63 (dd, 1H, J = 3.2,<br>9.4Hz), 6.89 (d, 1H, J = 9.4Hz), 7.27–7.38<br>(m, 5H) | (b) as C$_{21}$H$_{25}$NO$_3$<br>Calc.: 339.1831<br>Found: 339.1804 |
| 14 | R$^1$ = hydrogen | 85.7 | Oily substance | 1640 | 2.01–2.30 (m, 4H), 2.66–2.80 (m, 2H), | (a) as C$_{25}$H$_{27}$NO$_4$ |

TABLE 1-continued

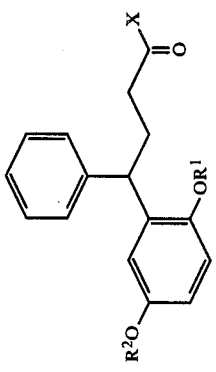

| Example No. | Compound | Yield % | Properties (Recrystallization solvent) | IR spectrum ($\nu_{max}$cm$^{-1}$) | NMR spectrum (CDCl$_3$,$\delta_{ppm}$) | (a) Elementary analysis or (b) High resolution mass spectrum |
|---|---|---|---|---|---|---|
| | $R^2$ = methyl X = 2-(4'-hydroxy) phenylethylamino | | | 3400 | 3.38–3.62 (m, 2H), 3.62 (s, 3H), 4.28–4.40 (t, 1H, J = 7.1Hz), 4.78–4.95 (br.s, 1H), 5.40–5.50 (m, 1H), 6.38 (d, 1H), J = 3.5Hz), 6.62 (dd, 1H, J = 3.5, 9.3Hz), 6.72 (d, 2H, J = 8.4Hz), 6.84 (d, 1H, J = 9.3Hz), 7.01 (d, 2H, J = 8.4Hz), 7.17–7.37 (m, 5H), 7.50–7.75 (br.s, 1H) | Calc.: C(%) 74.05 H(%) 6.71 N(%) 3.45<br>Found: 74.05 6.67 3.49 |
| 15 | $R^1$ = hydrogen $R^2$ = methyl X = N—[5-ethoxycarbonyl-2-(3'-methoxy) phenyloxy]phenylamino | 33.0 | m.p. 62.0–63.0° C. (acetone-petroleum ether) | 1603 1714 3300 | 1.48 (t, 3H, J = 6.6Hz), 2.30–2.60 (m, 4H), 3.15 (s, 3H), 3.31 (s, 3H), 4.36 (q, 2H, J = 6.6Hz), 4.43 (t, 1H, J = 7.7Hz), 6.50–7.00 (m, 9H), 7.10–7.40 (m, 5H), 7.70 (dd, 1H, J = 1.8, 8.1Hz), 7.85 (br.s, 1H), 9.06 (br.s, 1H) | (a) as C$_{33}$H$_{33}$NO$_7$<br>Calc.: C(%) 71.34 H(%) 5.99 N(%) 2.52<br>Found: 71.05 6.05 2.53 |
| 16 | $R^1$ = hydrogen $R^2$ = methyl X = adamantylamino | 46.2 | Oily substance | 1640 3140 | 1.50–2.30 (m,19H), 3.62 (s, 3H), 4.38 (t, 1H, J = 7.7Hz), 5.14 (br.s, 1H), 6.32 (d, 1H, J = 3.1Hz), 6.62 (dd, 1H, J = 3.1, 8.9Hz), 6.86 (d, 1H, J = 8.9Hz), 7.16–7.37 (m, 5H), 8.21 (s, 1H) *$\delta_{in}$d$_6$DMSO | (a) as C$_{27}$H$_{33}$NO$_3$<br>Calc.: C(%) 77.29 H(%) 7.93 N(%) 3.34<br>Found: 77.09 7.95 3.29 |
| 17 | $R^1$ = hydrogen $R^2$ = methyl X = 2-(3',4'-dihydroxyphenyl)-2-hydroxyethylamino | 74.8 | Oily substance | 1620 3350 | 1.90–2.26 (m, 4H), 2.86–3.24 (m, 2H), 3.62 (s, 3H), 4.20 (t, 1H, J = 7.4Hz), 4.31–4.42 (m, 1H), 5.12 (br.t, 1H), 6.46–6.80 (m, 6H), 7.05–7.35 (m, 5H), 7.72 (br.s, 1H), 8.66, 8.77, 8.85 (each 1H, s) | |
| 18 | $R^1$ = hydrogen $R^2$=methyl 8.46 X=N—methylhomopiperazinyl | 91.0 | m.p. 179.0–180.0° C. (ethanol-ether) | 1595 3200 | 1.70–2.0 (m, 2H), 2.20–2.40 (m, 4H), 2.36 (s, 3H), 2.45–2.75 (m, 4H), 3.20–3.60 (m, 3H), 3.62 (s, 3H), 3.80–4.00 (m, 1H), 4.40 (1H, J = 3.5Hz), 6.28 (d, 1H, J = 8.6Hz), 6.63 (dd, 1H, J = 3.1, 8.6Hz), 6.83 (d, 1H, J = 8.6Hz), 7.15–7.45 (m, 5H) | (a) as C$_{23}$H$_{30}$N$_2$O$_3$.HCl<br>C H N Cl (%) (%) (%) (%)<br>Calc.: 65.93 7.46 6.69<br>Found: 65.92 7.50 6.72 |
| 19 | $R^1$ = hydrogen $R^2$ = methyl X = 2-piperidino-ethylamino | 63.7 | Oily substance (hygroscopic) | 1640 3250 | 1.38–1.47 (m, 2H), 1.52–1.65 (m, 4H), 2.07–2.53 (m, 8H), 3.23–3.50 (m, 2H), 3.63 (s, 3H), 4.40 (t, 1H, J = 7.8Hz), 6.41 (br.t, 1H), 6.46 (d, 1H, J = 2.9Hz), 6.60 (dd, 1H, J = 2.9, 8.4Hz), 6.81 (d, 1H, J = 8.4Hz), 7.15–7.34 (m, 5H) | (b) as C$_{24}$H$_{32}$N$_2$O$_3$<br>Calc.: 396.2410<br>Found: 396.2372 |

4,766,116

TABLE 1-continued

[Structure: phenyl-CH(aryl)-CH2-CH2-C(=O)-X, where aryl is 2,5-disubstituted phenyl with OR¹ and OR²]

| Example No. | Compound | Yield % | Properties (Recrystallization solvent) | IR spectrum ($\nu_{max}$ cm$^{-1}$) | NMR spectrum (CDCl$_3$, $\delta_{ppm}$) | (a) Elementary analysis or (b) High resolution mass spectrum |
|---|---|---|---|---|---|---|
| 20 | R¹ = hydrogen; R² = methyl; X = 3-morpholino-propylamino | 68.1 | Oily substance (hygroscopic) | 1640, 3250 | 1.58–1.68 (m, 2H), 2.08–2.48 (m, 10H), 3.23–3.39 (m, 2H), 3.57–3.62 (m, 4H), 3.62 (s, 3H), 4.41 (t, 1H, J = 7.6Hz), 6.43 (d, 1H, J = 2.9Hz), 6.59 (dd, 1H, J = 2.9, 8.7Hz), 6.80 (d, 1H, J = 8.7Hz), 7.08 (br.t, 1H), 7.16–7.34 (m, 5H) | (b) as C$_{24}$H$_{32}$N$_2$O$_4$<br>Calc.: 412.2362<br>Found: 412.2893 |
| 21 | R¹ = hydrogen; R² = methyl; X = N-(2-oxo-2-pyrrolidinyl)ethylpiperazinyl | 94.6 | m.p. 139.0–141.0° C. (ethanol-ether) | 1620, 1640, 3180 | 1.68–2.02 (m, 4H), 2.13–2.41 (m, 4H), 2.41–2.66 (m, 4H), 3.26–3.55 (m, 8H), 3.61 (s, 3H), 3.55–3.88 (m, 2H), 4.34 (t, 1H, J = 6.0Hz), 6.29 (d, 1H, J = 3.5Hz), 6.62 (dd, 1H, J = 3.5, 9.3Hz), 6.86 (d, 1H, J = 9.3Hz), 7.14–7.47 (m, 5H), 8.54 (s, 1H) | (a) as C$_{27}$H$_{35}$N$_3$O$_4$·HCl<br>    C(%) H(%) N(%) Cl(%)<br>Calc.: 64.59 7.23 8.37 7.06<br>Found: 64.59 7.10 8.33 7.03 |
| 22 | R¹ = hydrogen; R² = methyl; X = 2-(2-indol-3-yl)ethylamino | 93.0 | | 1640, 3320 | 1.97–2.31 (m, 4H), 2.97 (t, 2H, J = 6.4Hz), 3.63 (s, 3H), 3.48–3.77 (m, 2H), 4.38 (t, 1H, J = 6.9Hz), 5.47–5.67 (m, 1H), 6.36 (d, 1H, J = 3.5Hz), 6.62 (dd, 1H, J = 3.5, 9.3Hz), 6.85 (d, 1H, J = 9.3Hz), 7.00 (br.s, 1H), 7.40–7.59 (m, 9H), 7.77 (s, 1H), 7.96 (br.s, 1H) | (a) as C$_{27}$H$_{28}$N$_2$O$_3$<br>    C(%) H(%) N(%)<br>Calc.: 75.67 6.59 6.54<br>Found: 75.68 6.53 6.44 |
| 23 | R¹ = hydrogen; R² = methyl; X = N-piperidinoamino | 94.7 | Oily substance (hydroscopic) | 1700, 3250 | 1.30–1.70 (m, 6H), 2.10–2.65 (m, 8H), 2.65–2.73 (br.t, 1H), 3.64 (s, 3H), 4.35–4.41 (t, 1H, J = 7.2Hz), 6.45 (d, 1H, J = 3.1Hz), 6.61 (dd, 1H, J = 3.1, 8.6Hz), 6.84 (d, 1H, J = 8.6Hz), 7.15–7.33 (m, 5H), 7.70–8.00 (br.s, 1H) | (b) as C$_{22}$H$_{28}$N$_2$O$_3$<br>Calc.: 368.2009<br>Found: 368.2114 |
| 24 | R¹ = hydrogen; R² = methyl; X = N-methyl-piperazinylamino | 71.0 | m.p. 145.0–147.0° C. (ethanol-ether) | 1655, 3100 | 1.9–2.9 (m, 13H), 2.3 (s, 3H), 3.63 (s, 3H), 4.38 (t, 1H, J = 7.4Hz), 6.45–6.80 (m, 3H), 7.1–7.4 (m, 5H) | (a) as C$_{22}$H$_{29}$N$_3$O$_3$·2HCl<br>    C(%) H(%) N(%) Cl(%)<br>Calc.: 57.89 6.85 9.21 15.54<br>Found: 57.66 6.83 9.02 15.38 |
| 25 | R¹ = hydrogen; R² = methyl | 90.2 | m.p. 169.0–170.0° C. (acetone-petroleum ether) | 1670, 3190 | 2.21–2.35 (m, 4H), 3.66 (s, 3H), 4.36 (t, 1H, J = 7.3Hz), 5.43 (br.s, 2H), 6.44 (d, 1H, J = 3.2Hz), 6.64 (dd, 1H, J = 3.2, 8.9Hz), 6.83 (d, LH, J = 8.9Hz), 7.20–7.37 (m, 5H) | (a) as C$_{17}$H$_{19}$NO$_3$<br>    C(%) H(%) N(%)<br>Calc.: 71.56 6.71 4.91<br>Found: 71.88 6.69 4.87 |
| 26 | X = amino; R¹ = hydrogen; R² = methyl | 69.7 | m.p. 148.0–150.0° C. (benzene) | 1635, 3300 | 2.0–2.25 (m, 4H), 3.28 (s, 3H), 3.59 (s, 3H), 4.41 (t, 1H, J = 7.4Hz), 6.28 (d, 1H, J = 3.1Hz), 6.61 (dd, 1H, J = 3.1, 9.4Hz), | (a) as C$_{24}$H$_{25}$NO$_3$<br>    C(%) H(%) N(%) |

TABLE 1-continued

[Structure: phenyl-CH(C6H3(OR1)(OR2))-CH2-CH2-C(=O)-X]

| Example No. | Compound | Yield % | Properties (Recrystallization solvent) | IR spectrum ($\nu_{max}$ cm$^{-1}$) | NMR spectrum (CDCl$_3$, $\delta$ ppm) | (a) Elementary analysis or (b) High resolution mass spectrum |
|---|---|---|---|---|---|---|
| 27 | X = N—methyl-N—phenyl R$^1$ = hydrogen R$^2$ = methyl | 77.2 | m.p. 110–111° C. (benzene) | 1640 1721 3300 3000 | 6.85 (d, 1H, J = 9.4Hz), 6.95–7.40 (m, 10H), 8.19 (br.s, 1H) 1.70–1.90 (m, 2H), 2.0–2.50 (m, 6H), 3.20–3.40 (m, 2H), 3.64 (s, 3H), 4.38 (t, 1H, J = 7.4Hz), 6.46 (d, 1H, J = 2.7Hz), 6.60 (dd, 1H, J = 2.7, 9.8Hz), 6.62 (t, 1H, J = 6.2Hz), 6.80 (d, 1H, J = 9.8Hz), 7.10–7.40 (m, 5H) | Calc.: Found: (a) as C$_{21}$H$_{25}$NO$_5$ C (%) H (%) N (%) 76.77 6.71 3.73 76.57 6.71 3.70<br>67.91 6.79 3.77 67.80 6.78 3.77 |
| 28 | X = 3-carboxypropylamino R$^1$ = hydrogen R$^2$ = methyl | 46.3 | m.p. 85.0–87.0° C. (benzene) | 1623 3200 | 2.20–2.40 (m, 4H), 2.70–2.90 (m, 4H), 3.20–3.40 (m, 2H), 3.62 (s, 3H), 3.50–3.75 (m, 2H), 4.32 (t, 1H, J = 7.8Hz), 6.33 (d, 1H, J = 3.9Hz), 6.63 (dd, 1H, J = 3.9, 9.8Hz), 6.84 (d, 1H, J = 9.8Hz), 7.15–7.40 (m, 5H) | (a) as C$_{21}$H$_{26}$N$_2$O$_3$ C (%) H (%) N (%) Calc.: 71.16 7.39 7.90 Found: 71.16 7.21 7.93 |
| 29 | X = piperazinyl R$^1$ = hydrogen R$^2$ = methyl | 15.5 | m.p. 220–222° C. (benzene) | 1626 1617 3300 | 2.15–2.45 (m, 8H), 3.15–3.40 (m, 4H), 3.45–3.75 (m, 4H), 4.29 (t, 2H, J = 7.4Hz), 6.32 (d, 2H, J = 3.1Hz), 6.62 (dd, 2H, J = 8.7, 3.1Hz), 6.83 (d, 2H, J = 8.7Hz), 7.15–7.40 (m, 10H), 7.80–8.00 (br, s, 2H) | (a) as C$_{38}$H$_{42}$N$_2$O$_6$ C (%) H (%) N (%) Calc.: 73.29 6.80 4.50 Found: 73.29 6.73 4.39 |
| 30 | X = N—4-(2'-hydroxy-5'-methoxyphenyl-4-phenyl-1-oxo butylpiperazinyl R$^1$ = hydrogen R$^2$ = methyl | 35.1 | m.p. 165.0–166.0° C. (benzene) | 1591 3160 | 1.60–1.90 (m, 2H), 2.20–2.40 (m, 4H), 2.75–3.10 (m, 4H), 3.2–3.55 (m, 2H), 3.62 (s, 3H), 3.70–4.00 (m, 2H), 4.30–4.50 (m, 1H), 6.25–6.35 (d, 1H, J = 3.1Hz), 6.55–6.65 (dd, 1H, J = 3.1, 9.0Hz), 6.80–6.90 (d, 1H, J = 9.0Hz), 7.15–7.45 (m, 5H) | (a) as C$_{22}$H$_{28}$N$_2$O$_3$ C (%) H (%) N (%) Calc.: 71.71 7.66 7.60 Found: 71.71 7.52 7.85 |
| 31 | X = homopiperazinyl R$^1$ = hydrogen R$^2$ = methyl | 31.0 | m.p. 224–225° C. (benzene) | 1615 3200 | 1.55–1.85 (m, 2H), 2.05–2.40 (m, 8H), 3.1–4.0 (m, 8H), 3.61 (s, 3H), 3.63 (s, 3H), 4.10–4.35 (m, 2H), 6.20–6.30 (m, 2H), 6.55–6.65 (m, 2H), 6.80–6.90 (m, 2H), 7.10–7.40 (m, 10H), 8.00–8.40 (br.s, 2H) | (a) as C$_{39}$H$_{44}$N$_2$O$_6$ C (%) H (%) N (%) Calc.: 73.56 6.97 4.40 Found: 73.32 7.02 4.30 |
| 32 | X = N—[4-(2'-hydroxy-5-methoxy)phenyl-4-phenyl-1-oxobutyl R$^1$ = hydrogen R$^2$ = methyl | 26.0 | m.p. 70–72° C. (ethanol-ether) | 1642 3160 | 2.1–2.6 (m, 10H), 2.75–3.10 (m, 4H), 3.30–3.40 (m, 2H), 3.66 (s, 3H), 4.00–4.60 (br, 2H), 4.38 (t, 1H, | (a) as C$_{23}$H$_{31}$N$_3$O$_3$·HCl C H N Cl (%) (%) (%) (%) |

TABLE 1-continued

[Structure: R²O-phenyl (with OR¹ substituent) -CH(phenyl)-CH₂-CH₂-C(=O)-X]

| Example No. | Compound | Yield % | Properties (Recrystallization solvent) | IR spectrum ($\nu_{max}$ cm$^{-1}$) | NMR spectrum (CDCl₃, $\delta_{ppm}$) | (a) Elementary analysis or (b) High resolution mass spectrum |
|---|---|---|---|---|---|---|
| 33 | X = 2-(piperazinyl) ethylamino R¹ = hydrogen R² = methyl | 18.0 | m.p. 130–131.0° C. (ethanol-ether) | 1642 3300 | J = 7.5Hz), 6.10 (t, 1H, J = 5.5Hz), 6.50 (d, 1H, J = 3.2Hz), 6.61 (dd, 1H, J '2, 3.2 8.9Hz), 6.84 (d, 1H, J = 8.9Hz), 7.2-7.4 (m, 5H) 2.1–2.6 (m, 14H), 3.2–3.45 (m, 4H), 3.62 (s, 3H), 3.64 (s, 3H), 3.5-3.75 (m, 2H), 4.32 (t, 1H, J = 7.1Hz), 4.39 (t, 1H, J = 7.5Hz), 5.97 (t, 1H, J = 4.2Hz), 6.29 (d, 1H, J = 2.6Hz), 6.42 (d, 1H, J = 2.6Hz), 6.55–6.70 (m, 2H), 6.8–6.9 (m, 2H), 7.15–7.40 (m, 10H) | (a) as C₄₀H₄₇N₃O₆·HCl Calc.: C 58.72 H 7.07 N 8.93 Cl 15.07 (%) Found: 58.80 7.20 8.86 14.87 (%) Calc.: 68.41 6.89 5.98 5.05 (%) Found: 68.41 6.74 5.96 5.25 (%) |
| 34 | X = N—[4-(2'-hydroxy-5'-methoxy)phenyl-4-phenyl-1-oxobutyl] piperazinyl ethyl-amino R¹ = acetyl R² = methyl | 95.0 | m.p. 105.0–106.0° C. (benzene-petroleum ether) | 1640 1760 | 2.10–2.45 (m, 8H), 2.22 (s, 3H), 2.28 (s, 3H), 3.30 (m, 2H), 3.52–3.67 (m, 2H), 3.77 (s, 3H), 4.10 (t, 1H, J = 6.5Hz) 6.76 (dd, 1H, J = 3.4, 9.1Hz), 6.84 (d, 1H, J = 3.4Hz), 6.92 (d, 1H, J = 9.1Hz), 7.10–7.33 (m, 5H) | (a) as C₂₄H₃₀N₂O₄ C(%) H(%) N(%) Calc.: 70.22 7.37 6.82 Found: 70.03 7.46 6.81 |
| 35 | X = N—methylpiperazinyl R¹ = R² = methyl X = N—methylpiperadizinyl | 49.1 | m.p. 189.0–191.5° C. (ethanol-ether) | 1649 | 2.20–2.40 (m, 8H), 2.27 (s, 3H), 3.25–3.35 (m, 2H), 3.55–3.65 (m, 2H), 3.71 (s, 3H), 3.73 (s, 3H), 4.37 (t, 1H, J = 7.5Hz), 6.68 (dd, 1H, J = 3.2, 8.6Hz), 6.76 (d, 1H, J = 8.6Hz), 6.82 (d, 1H, J = 3.2Hz), 7.10–7.35 (m, 5H) | (a) as C₂₃H₃₀N₂O₃·HCl C H N Cl (%) (%) (%) (%) Calc.: 65.93 7.46 6.69 8.46 Found: 65.73 7.63 6.58 8.32 |
| 36 | R¹ = hydrogen R² = methyl X = 2-(N—dimethylamino) ethyloxy | 80.6 | Oily substance | 1740 3300 | 2.15–2.47 (m, 4H), 2.35 (s, 6H), 2.53–2.69 (m, 2H), 3.68 (s, 3H), 3.94–4.02 (m, 1H), 4.36–4.44 (m, 1H), 4.51 (dd, 1H, J = 8.4, 6.8Hz), 6.58 (d, 1H, J = 3.6Hz), 6.60 (dd, 1H, J = 3.6, 8.7Hz), 6.71 (d, 1H, J = 8.7Hz), 7.13–7.34 (m, 5H) | (b) as C₂₁H₂₇NO₄ Calc.: 357.1937 Found: 357.1937 |

Reference Example 1

Preparation of 7-methoxy-5-phenyl-2-oxo-2,3,4,5-tetrahydro-1-benzoxepin

A 28.6 g (0.1 mol) amount of 4-(4'-methoxy)-phenyloxy-4-phenyl butyric acid was mixed with 350 g of 75% polyphosphoric acid and the mixture was then stirred at room temperature for 5 hours. The reaction solution was then poured into ice water and was extracted with ether. The ether layer was washed with a 2N aqueous sodium hydroxide solution and subsequently with water, followed by drying. After concentration, the desired compound was obtained in 30% yield.

Reference Example 2

A 12.4 g (0.1 mol) amount of 4-methoxyphenol and 16.2 g (0.1 mol) of γ-phenyl-γ-butyrolactone were stirred at room temperature for 5 hours in 300 g of 75% polyphosphoric acid. The reaction mixture was treated in the same manner as in Reference Example 1. Thus, the desired compound was obtained in 30% yield. The physical properties of the resultant compounds are as follows:

m.p.: 65.0° C.–67.0° C. (recrystallization from ethanol)

IR spectrum (KBr cm$^{-1}$): 1760

NMR spectrum (CDCl$_3$, δppm): 2.33–2.70 (m, 4H) 3.65 (s, 3H), 4.40 (dd, 1H, J=6.5, 13.0 Hz) 6.28 (d, 1H, J=3.05 Hz) 6.73 (dd, 1H, J=3.05, 8.71 Hz) 7.05 (d, 1H, J=8.71 Hz) 7.23–7.47 (m, 5H)

Reference Example 3

Preparation of 4-(4'-methoxy)phenyloxy-4-phenyl-n-butyric acid.

A 24.8 g (0.2 mol) amount of p-methoxyphenol was dissolved in 38.6 ml of commercially available 28% sodium methoxide in methanol. The solution was heated under reflux for one hour and 48.6 g (0.3 mol) of γ-phenyl-γ-butyrolactone was added thereto. The reaction mixture was heated to a temperature of 150° C. to 160° C. in an oil bath. Thus, the methanol was distilled off and the reaction mixture was concentrated. The residue was heated at the same temperature for 4 hours and a 2N aqueous sodium hydroxide solution was added thereto. Thus, the residue was dissolved. After cooling, the aqueous layer was extracted with ether and the extract was acidified with 2N hydrochloric acid. Thus, the product was precipitated. After filtration and washing with water, the product was recrystallized from ethanol. As a result, 48.6 g (85% yield) of the desired compound was obtained. The physical properties of the resultant compounds are as follows:

m.p.: 67° C.–68° C.

IR spectrum (KBr, cm$^{-1}$): 1760, 3380

NMR spectrum (CDCl$_3$, δppm): 2.12–2.33 (m, 2H) 2.47 (m, 2H), 3.77 (s, 3H) 5.09 (dd, 1H, J=5.0, 8.0 Hz), 6.67–6.86 (m, 4H) 7.22–7.41 (m, 5H)

High resolution mass spectrum (as C$_{17}$H$_{18}$O$_4$): Calc.: 286.1205. Found: 286.1225.

Evaluation Example

Various activities of certain compounds prepared in the above-mentioned Synthesis Examples were evaluated as follows. The toxicity (i.e., 50% lethal dose LD$_{50}$) of the compounds according to the present invention was 110 to 500 mg/kg or more when the so-called up-and-down method, in which the sample compound was intraperitoneally injected into ddY-STF mice, was used.

1. Global Ischemia Activity

Male ddY mice having a body weight of 22 to 30 g were used (i.e., 6 mice in one group). The sample compound prepared in the Synthesis Example 1 or 7 was intraperitoneally injected into the mice and the mice were decapitated 30 minutes after the injection. After decapitation, the gasping times were determined. The results were compared with a control group to which only the saline was injected.

| Compound | Global Ischemia ED$_{min}$* (mg/kg, ip) |
| --- | --- |
| Example 1 | 25 |
| Example 7 | 50 |

*Minimum effective dose

In addition, when the compounds obtained in the Synthesis Example Nos. 6, 15, 19, 30, 32, and 33 were injected at a dose of 50 mg/kg or less, there was a significant difference in the extension of the gasping time.

2. Hypobaric Hypoxia Activity

Male ddY mice having a body weight of 22 to 30 g were used (i.e., 7 to 10 mice in one group). The mice were placed in a desiccator having a volume of about 1 liter and the desiccator was evacuated and adjusted by a vacuum pump to a pressure of 180 mmHg. Then, the sample compound prepared in the Synthesis Example 1 or 7 was intraperitoneally injected into the mice. The desiccator was evacuated 30 minutes after the injection and the time from the start of the evacuation to the termination of breathing by the mice was determined to be the survival time. If a mouse was still alive 15 minutes after exposure to the hypoxia, the survival time was assumed to be 15 minutes. The results were compared with a control group, to which only the physiological saline was injected.

| Compound | Hypobaric Hypoxia ED$_{min}$*1 (mg/kg, ip) |
| --- | --- |
| Example 1 | 50 |
| Example 7 | 50 |

*1 Minimum effective dose

In addition, when the compound obtained in the Synthesis Example No. 33 was injected at a dose of 50 mg/kg or less, there was a significant difference in the extension of the survival time. However, the compound obtained in the Synthesis Example 19 reduced the survival time, compared with the control group.

3. Normobaric Hypoxia Activity

Male ddY mice having a body weight of 22 to 30 g were used (i.e., 7 to 10 mice in one group). The sample compound prepared in the Synthesis Example 1 or 7 was intraperitoneally injected into the mice and, 30 minutes later, the mice were placed in a desiccator having a volume of about 1 liter and filled with a gas mixture of 96% N$_2$ and 4% O$_2$. The survival time up to the termination of breathing by the mice was determined. During the test, the N$_2$—O$_2$ gas mixture was continuously supplied at a rate of 3 l/min. When the survival time was more than 15 minutes, the survival time was assumed to be 15 minutes. The results were compared with a control group, to which only a physiological saline was injected.

| Compound | Normobaric Hypoxia $ED_{min}$* (mg/kg, ip) |
| --- | --- |
| Example 1 | 50 |
| Example 7 | Inactive at 50 mg/kg, ip |

*Minimum effective dose

4. Hemicholinium No. 3 (HC-3) Induced Anoxia Activity

Male mice having a body weight of 22 to 30 g were used (i.e., 7 to 10 mice in one group). The sample compound prepared in the Synthesis Example 1 or 7 was intraperitoneally injected into the mice and, 15 minutes later, 5 mg/kg of hemicholinium No. 3 was injected into the tail vein of the mice. The time from the injection of hemicholinium No. 3 to the termination of breathing by the mice was determined to be the survival time. The results were compared with that of a control group to which only a physiological saline was injected.

| Compound | HC-3 Induced Anoxia $ED_{min}$* (mg/kg, ip) |
| --- | --- |
| Example 1 | 50 |
| Example 7 | 25 |

*Minimum effective dose

5. Antilipid Peroxidation Activity (A) Male Wister rats having a body weight of 350 to 380 g were used. A rat was decapitated and the whole brain other than the cerebellum was homogenized in 10 times volume of ice cooled 50 mM buffered saline (PBS) having a pH of 7.4. The homogenized mixture was then centrifugally separated and the resultant supernatant frozen at a temperature of −30° C. The frozen specimen was melted in flowing water and was then diluted with 3 times volume PBS to prepare the diluted homogenate.

A 10 μl of a solution of the sample compound prepared in the Synthesis Example 1 or 7 was added to 1 ml of the diluted homogenate obtained above and the mixture was incubated at a temperature of 37° C. for 30 minutes. Thereafter, 200 μl of an ice cooled 35% HClO$_4$ solution was added and the mixture was shaken to terminate the reaction. The mixture was centrifugally separated for 10 minutes at 3,000 rpm. A 0.5 ml amount of the resultant supernatant was used for the so-called TBA reaction (see: H. Ohkawa, N. Ohishi, and K. Yagi, Anal. Biochem., 95, 351 (1979)).

The reaction mixture contained 0.5 ml of the supernatant, 0.2 ml of 0.2% SDS, 1.5 ml of 20% NaOAc, 1.5 ml of 0.8% TBA, and 0.3 ml of H$_2$O.

As is the case of the test compound solution, 10 μl of the standard solution of tetramethoxypropane (TMP) was prepared and was added to the reaction mixture in amounts of 0 to 10 nmole/tube. The reaction mixture was heated to a temperature of 95° C. for 60 minutes in a water bath. After cooling, 1 ml of water and 5 ml of a mixed solvent of butanol and pyridine (15:1) was added. The extraction was effected for 5 minutes in a shaking machine. Thereafter, the resultant layers were stabilized for 10 minutes at 2,000 rpm and the absorbance of the organic layer at 532 nm or the fluorescence intensity of the organic layer at 553 nm (excited at 515 nm) were determined. The lipid peroxide content was determined and represented a nmole number of malon dialdehyde (MDA) per mg of protein. The protein was determined by a Lawry method (i.e., Lawry et al., J. Biol. Chem., 193, 265 (1951)).

The results are as follows.

| Compound | Antilipid Peroxidation* |
| --- | --- |
| 1 | 95.4 |
| 7 | 88.0 |

*% inhibition of the rat brain homogenate at $10^{-4}$M (B) Male ddY mice having a body weight of 24 to 27 g were used (i.e., 5 to 9 mice in one group). After 16 to 17 hours nestia, 85 mg/kg of alloxan was rapidly injected into the tail vein of the mice. After injecting the alloxan, the mice were subjected to free feeding and free water intaking and, 24 hours later, the sample compound was intraperitoneally injected into the mice. After an additional 24 hours, anesthesia was applied to the mice with ether and the blood of alvine aorta and cava was sampled. The amounts of the lipid peroxides in the blood serum were quantitatively measured according to a Yagi's method (i.e., K. Yagi, Biochem. Med., 15, 212, 1976).

The results were compared with that of a control group to which only a physiological saline was injected.

As a result, at a dose of 50 mg/kg, the compounds of the Synthesis Examples 3, 12, 13, 18, 28, 31, and 33 made a significant difference in the inhibition of the formation of the lipid peroxides. The compounds of the synthesis Examples 1, 4, 6, 9, 29, and 36 caused inhibition at a dose of 10 mg/kg, and the compounds of the Synthesis Examples 8 and 16 caused inhibition at a dose of 5 mg/kg.

6. Scopolamine Amnesia Activity

Ten male ddY mice having a body weight of 22 to 30 g were used as one group. A slit was located between a light room and a dark room. In the dark room, an arrangement was made whereby an electric shock was given to the feet by an electric current. Thus, the behavior of the mice in relation to step-through to the dark room was studied. The mice were amnesically treated with an administration of scopolamine with or without the injection of the sample compound 1 or 7 and the time taken to avoid step-through by the mice to the dark room was determined by the so-called step-through passive avoidance learning method. The electric current used was 0.6 mA. The scopolamine was hypodermically injected in an amount of 0.5 mg/kg at 20 minutes prior to the first session and the sample compound was intraperitoneally injected immediately after the first session. The retention test (i.e., the second session) was carried out 24 hours later.

The results are as follows.

| Compound | Scopolamine Amnesia $ED_{min}$* (mg/kg, ip) |
| --- | --- |
| 1 | 50 |
| 7 | 25 |

*Minimum effective dose

7. Preliminary Acute Toxicity Test

Male ddY mice having a body weight of 22 to 30 g were used (i.e., 5 mice in one group). The sample compound prepared in the Synthesis Example 1 or 7 was intraperitoneally injected in a dose of 100 mg/kg, 200 mg/kg, or 500 mg/kg. None of the mice died.

We claim:

1. A diaryl butyric acid derivative having the general formula:

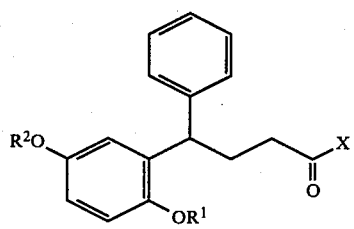

wherein
R$^1$ represents a hydrogen atom, an alkyl group having 1 to 3 carbon atoms, or an acyl group having 2 to 4 carbon atoms;
R$^2$ represents an alkyl group having 1 to 3 carbon atoms; and
X represents a pyrrolidinyl group, a morpholino group, a thiomorpholino group, an amino group, a group having the general formula:

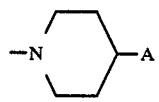

wherein A represents a hydrogen atom or an alkyl group having 1 to 3 carbon atoms,
a group having the general formula:

wherein J represents a phenyl group, a benzyl group, a aralkyl group having 7 to 9 carbon atoms substituted with at least one hydroxyl group,
a group having the general formula:

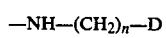

wherein n is an integer of 0 to 5, D represents a saturated crosslinked ring type hydrocarbon group, a piperidinyl group, a morpholino group, a thiomorpholino group, a pyridyl group, an indolyl group, a piperazinyl group, a pyrrolidinyl group, a carboxyl group, a phenyl group substituted with a hydroxyl, or aryloxy group, an N-[4-(2'-hydroxy-5'-methoxy)phenyl-4-phenylbutyryl]piperazinyl group, or a piperazinyl group having an alkyl group with 1 to 3 carbon atoms substituted for the hydrogen atom on the nitrogen atom,
a group having the general formula:

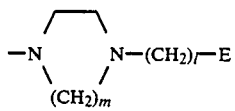

wherein m is 2 or 3, l is an integer of 0 to 4, E is a hydrogen atom, a phenyl group, a hydroxyl group, a pyrrolidinecarbonyl group, a 4-(4'-methoxyphenyl)-4-phenylbutylamide group, or a 4-(2'-hydroxy-5'-methoxy)phenyl-4-phenylbutyryl group,
a group having the general formula:

wherein p is an integer of 2 to 4, and L represents a dialkylamino group having a C$_1$ to C$_3$ alkyl group, or
a group having the general formula:

wherein G represents an aralkyl group having 8 to 9 carbon atoms substituted with at least two hydroxyl groups;
or the pharmaceutically acceptable salt thereof.

2. A diaryl butyric acid derivative as claimed in claim 1, wherein R$^1$ is a hydrogen atom and R$^2$ is a methyl group.

3. A diaryl butyric acid derivative as claimed in claim 1, wherein R$^1$ is an acetyl group and R$^2$ is a methyl group.

4. A diaryl butyric acid derivative as claimed in claim 1, wherein both R$^1$ and R$^2$ are a methyl group.

5. A method for treating cerebral organic disorders and pathergasia, said method comprising administering an effective amount to treat cerebral organic disorders and pathergasia of a diaryl butyric acid derivative having the general formula:

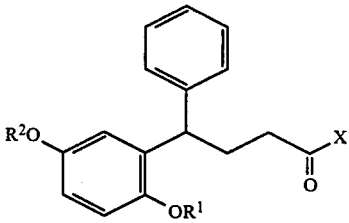

wherein R$^1$ represents a hydrocarbon atom, an alkyl group having 1 to 3 carbon atoms, or an acyl group having 2 to 4 carbon atoms; R$^2$ represents an alkyl group having 1 to 3 carbon atoms; and X represents a pyrrolidinyl group, a morpholino group, a thiomorpholino group, an amino group, a group having the general formula:

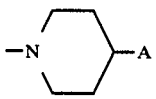

wherein A represents a hydrogen atom or an alkyl group having 1 to 3 carbon atoms,
a group having the general formula:

$$\begin{array}{c} CH_3 \\ | \\ -N-J \end{array}$$

wherein J represents a phenyl group, a benzyl group, an aralkyl group having 7 to 9 carbon atoms substituted with at least one hydroxyl group,
a group having the general formula:

—NH—(CH$_2$)$_n$—D wherein n is an integer of 0 to 5, D represents a saturated crosslinked ring type hydrocarbon group, a piperidinyl group, a morpholino group, a thiomorpholine group, a pyridyl group, an indolyl group, a piperazinyl group, a pyrrolidinyl group, a carboxyl group, a phenyl group substituted with a hydroxyl, or aryloxy group, an N-[4-(2'-hydroxy-5'-methoxy)phenyl-4-phenylbutyryl]piperazinyl group, or a piperazinyl group having an alkyl group with 1 to 3 carbon atoms substituted for the hydrogen atom on the nitrogen atom, $$-N \underset{(CH_2)_m}{\overset{\diagup \diagdown}{\diagdown \diagup}} N-(CH_2)_l-E$$

wherein m is 2 or 3, l is an integer of 0 to 4, E is a hydrogen atom, a phenyl group, a hydroxyl group, a pyrrolidinecabonyl group, a 4-(4,'-methoxyphenyl)-4-phenylbutylamide group, or a 4-(2'-hydroxy-5'-methoxy)phenyl-4-phenylbutyryl group,
a group having the general formula:

—O—(CH$_2$)$_p$—L wherein p is an integer of 2 to 4, and L represents a dialkylamino group having a $C_1$ to $C_3$ alkyl group, or
a group having the general formula:

$$\begin{array}{c} H \\ | \\ -N-G \end{array}$$

wherein G represents an aralkyl group having 8 to 9 carbon atoms substituted with at least two hydroxyl groups;
or the pharmaceutically acceptable salt thereof and a pharmaceutically acceptable carrier therefor.

6. The method as claimed in claim 5, wherein $R^1$ is a hydrogen atom and $R^2$ is a methyl group.

7. The method as claimed in claim 5, wherein $R^1$ is an acetyl group and $R^2$ is a methyl group.

8. The method as claimed in claim 5, wherein both $R^1$ and $R^2$ are a methyl group.

9. A pharmaceutial composition of matter for treating cerebral organic disorders and pathergasia, said composition comprising an effective amount to treat cerebral organic disorders and pathergasia of a diaryl butyric acid derivative having the general formula:

wherein $R^1$ represents a hydrogen atom, an alkyl group having 1 to 3 carbon atoms, or an acyl group having 2 to 4 carbon atoms; $R^2$ represents an alkyl group having 1 to 3 carbon atoms; and X represents a pyrrolidinyl group, a morpholino group, a thiomorpholino group, an amino group, a group having the general formula:

wherein A represents a hydrogen atom or an alkyl group having 1 to 3 carbon atoms,
a group having the general formula:

$$\begin{array}{c} CH_3 \\ | \\ -N-J \end{array}$$

wherein J represents a phenyl group, a benzyl group, aralkyl group having 7 to 9 carbon atoms substituted with at least one hydroxyl group,
a group having the general formula:

—NH—(CH$_2$)$_n$—D wherein n is an integer of 0 to 5, D represents a saturated crosslinked ring type hydrocarbon group, a piperidinyl group, a morpholino group, a thiomorpholino group, a pyridyl group, an indolyl group, a piperazinyl group, a pyrrolidinyl group, a carboxyl group, a phenyl group substituted with a hydroxyl, or aryloxy group, an N-[4-(2'-hydroxy-5'-methoxy)phenyl-4-phenylbutyryl]piperazinyl group, or a piperazinyl group having an alkyl group with 1 to 3 carbon atoms substituted for the hydrogen atom on the nitrogen atom, $$-N \underset{(CH_2)_m}{\overset{\diagup \diagdown}{\diagdown \diagup}} N-(CH_2)_l-E$$

wherein m is 2 or 3, l is an integer of 0 to 4, E is a hydrogen atom, a phenyl group, a hydroxyl group, a pyrrolidine cabonyl group, a 4-(4'-methoxyphenyl)-4-phenylbutylamide group, or a 4-(2'-hydroxy-5'-methoxy)phenyl-4-phenylbutyryl group,
a group having the general formula:

—O—(CH$_2$)$_p$—L wherein p is an integer of 2 to 4, and L represents a dialkylamino group having a $C_1$ to $C_3$ alkyl group, or
a group having the general formula:

wherein G represents an aralkyl group having 8 to 9 carbon atoms substituted with at least two hydroxyl groups;
or the pharmaceutically acceptable salt thereof and a pharmaceutically acceptable carrier therefor.

10. The composition as claimed in claim 9, wherein $R_1$ is a hydrogen atom and $R_2$ is a methyl group.

11. The composition as claimed in claim 9, wherein $R_1$ is an acetyl group and $R_2$ is a methyl group.

12. The composition as claimed in claim 9, wherein both $R_1$ and $R_2$ are a methyl group.

* * * * *